(12) United States Patent
Vrabec et al.

(10) Patent No.: US 11,617,884 B2
(45) Date of Patent: Apr. 4, 2023

(54) ELECTRICALLY ANESTHETIZING A PERIPHERAL NERVE WITH ON-DEMAND ELECTRICAL NERVE BLOCK FOR CHRONIC PAIN MANAGEMENT

(71) Applicant: Case Western Reserve University, Cleveland, OH (US)

(72) Inventors: Tina L. Vrabec, Willoughby Hills, OH (US); Kevin L. Kilgore, Avon Lake, OH (US); Jesse S. Wainright, Willoughby Hills, OH (US); Niloy Bhadra, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 289 days.

(21) Appl. No.: 16/820,035

(22) Filed: Mar. 16, 2020

(65) Prior Publication Data

US 2020/0289817 A1 Sep. 17, 2020

Related U.S. Application Data

(60) Provisional application No. 62/818,857, filed on Mar. 15, 2019.

(51) Int. Cl.
*A61N 1/20* (2006.01)
*A61N 1/05* (2006.01)

(52) U.S. Cl.
CPC .............. *A61N 1/20* (2013.01); *A61N 1/0551* (2013.01)

(58) Field of Classification Search
CPC ...... A61N 1/20; A61N 1/0551; A61N 1/3756; A61N 1/3787; A61N 1/36071; A61N 1/37205
See application file for complete search history.

(56) References Cited

U.S. PATENT DOCUMENTS 7,801,602 B2 * 9/2010 McClure .............. A61N 1/3787
607/2
8,423,146 B2 4/2013 Giftakis et al.
(Continued)

FOREIGN PATENT DOCUMENTS

WO 2015/095880 A2 6/2015

OTHER PUBLICATIONS

Ackermann Jr, D. Michael, et al. "Separated interface nerve electrode prevents direct current induced nerve damage." Journal of neuroscience methods 201.1 (2011): 173-176.
(Continued)

*Primary Examiner* — Mark W. Bockelman
(74) *Attorney, Agent, or Firm* — Tarolli, Sundheim, Covell & Tummino LLP

(57) ABSTRACT

Chronic pain management can be achieved by electrically anesthetizing a peripheral nerve with on-demand electrical nerve block (OD-ENB). OD-ENB can be provided by an implantable capsule. Externally, at least a portion of the capsule can be constructed of a conductive membrane and the rest of the capsule comprises a biocompatible material. A blocking electrode contact, a return electrode contact, and a powering/communication component can be within the capsule. The blocking electrode contact can deliver a direct current (DC) through a portion of the conductive membrane to block conduction in the neural tissue to provide the OD-ENB. The return electrode contact can receive a return current from the neural tissue through another portion of the conductive membrane. The powering/communication component can communicate with one or more external components located external to the patient's body to receive a power signal. Notably the capsule has no internal battery.

16 Claims, 2 Drawing Sheets

(56) References Cited

U.S. PATENT DOCUMENTS

| | | |
|---|---|---|
| 9,008,800 B2 | 4/2015 | Ackermann, Jr. et al. |
| 2016/0051813 A1* | 2/2016 | Faltys ................. A61N 1/3756 607/118 |
| 2017/0050024 A1 | 2/2017 | Bhadra et al. |
| 2018/0280691 A1* | 10/2018 | Ackermann ............. A61N 1/20 |
| 2019/0282814 A1 | 9/2019 | Schepis et al. |
| 2019/0357847 A1 | 11/2019 | Franke et al. |

OTHER PUBLICATIONS

Bartsch, T., and P. J. Goadsby. "Increased responses in trigeminocervical nociceptive neurons to cervical input after stimulation of the dura mater." Brain 126.8 (2003): 1801-1813.

Bhadra, Niloy, and Kevin L. Kilgore. "Direct current electrical conduction block of peripheral nerve." IEEE Transactions on Neural Systems and Rehabilitation Engineering 12.3 (2004): 313-324.

Bogduk, Nikolai. "The neck and headaches." Neurologic clinics 22.1 (2004): 151-171.

Busch, V., et al. "Occipital nerve blockade in chronic cluster headache patients and functional connectivity between trigeminal and occipital nerves." Cephalalgia 27.11 (2007): 1206-1214.

Cogan, Stuart F. "Neural stimulation and recording electrodes." Annu. Rev. Biomed. Eng. 10 (2008): 275-309.

Defrin, Ruth. "Chronic post-traumatic headache: clinical findings and possible mechanisms." Journal of Manual & Manipulative Therapy 22.1 (2014): 36-43.

Falinower, S. Y. L. V. A, I. N., et al. "A C-fiber reflex modulated by heterotopic noxious somatic stimuli in the rat." Journal of neurophysiology 72.1 (1994): 194-213.

Inan, N., et al. "C2/C3 Ne rve Blocks and Greater Occipital Nerve Block in Cerv icogenic Headache Treatment." Functional neurology 16.3 (2001): 239-243.

McCall, Robert B. "Trigeminal ganglion elicited increases in nucleus trigeminal caudaiis blood flow: a novel migraine model." Brain research 775.1-2 (1997): 189-192.

Merrill, Daniel R., Marom Bikson, and John GR Jefferys. "Electrical stimulation of excitable tissue: design of efficacious and safe protocols." Journal of neuroscience methods 141.2 (2005): 171-198.

Mortimer, J. Thomas, David Kaufmau, and Uros Roessmann. "Intramuscular electrical stimulation: tissue damage." Annals of biomedical engineering 8.3 (1980): 235-244.

Naja, Zoher M., et al. "Occipital nerve blockade for cervicogenic headache: a double-blind randomized controlled clinical trial." Pain practice 6.2 (2006): 89-95.

Vrabec, Tina, et al. "Characterization of high capacitance electrodes for the application of direct current electrical nerve block." Medical & biological engineering & computing 54.1 (2016): 191-203.

Yang, Fei, et al. "Differential expression of voltage-gated sodium channels in afferent neurons renders selective neural block by ionic direct current." Science advances 4.4 (2018): eaaq1438.

Youn, Dong-ho. "Trigeminal long-term potentiation as a cellular substrate for migraine." Medical Hypotheses 110 (2018): 27-30.

* cited by examiner

ELECTRICALLY ANESTHETIZING A PERIPHERAL NERVE WITH ON-DEMAND ELECTRICAL NERVE BLOCK FOR CHRONIC PAIN MANAGEMENT

RELATED APPLICATIONS

This application claims priority to U.S. Provisional Application Ser. No. 62/818,857, filed Mar. 15, 2019, entitled "ELECTRICALLY ANESTHETIZING A PERIPHERAL NERVE FOR THE TREATMENT OF CHRONIC PAIN AND OTHER DISORDERS". The entirety of this provisional application is hereby incorporated by reference for all purposes.

TECHNICAL FIELD

The present disclosure relates generally to chronic pain management and, more specifically, to electrically anesthetizing a peripheral nerve with on-demand electrical nerve block (OD-ENB) for chronic pain management (and/or the treatment of other disorders).

BACKGROUND

Chronic pain management is a complicated and highly patient specific area of medicine. One example of a disorder that causes chronic pain is Knee Osteoarthritis (KOA), a degenerative joint disease, common in both the elderly and in the obese. Conservative treatments for KOA include weight loss, exercise, analgesics, intra-articular steroid injections and physical therapy. More radical treatments include surgical interventions, like knee arthroplasty, which can itself result in significant persistent pain. Moreover, there are many patients that are non-responsive to the conservative treatment, but are not good surgical candidates because of medical comorbidities and/or a high body mass index (BMI). Such KOA patients are highly susceptible to chronic opioid use. The use of opioids for chronic pain has led to a nationwide epidemic of addition resulting, in the implosion of families and communities.

Accordingly, clinicians seek alternative interventions in patients that have failed conservative therapy and/or in patients in which surgical interventions do not work. One option for these patients is genicular nerve block (GNB) targeting the sensory and motor nerves to the structures around the knee with an injection of corticosteroid and local anesthetic under ultrasound guidance. In such patients, improvements can be seen for up to six months post-injection and the procedure can be repeated, but only at a physician's office. Another option for these patients is radiofrequency ablation of the genicular nerves, but each patient has different outcomes and the progression of their disease and recovery from the ablation procedure is highly individualized. These treatment modalities are ill suited to address the needs of patients in terms of adequate pain relief, quality of life, and convenience, making patients feel as if their pain management is out of their control.

SUMMARY

The present disclosure relates to electrically anesthetizing a peripheral nerve with on-demand electrical nerve block (OD-ENB) for chronic pain management (and/or the treatment of other disorders). OD-ENB is a patient-specific intervention that can be adjusted over time to provide sustained relief for a long period of time and is customizable for the individual patient, giving patients control of their pain management without opioids.

In an aspect, the present disclosure can include a system that can be used to electrically anesthetize a peripheral nerve with on-demand electrical nerve block (OD-ENB) for chronic pain management. The system can include a power source and an implantable capsule. At least a portion of the capsule can be constructed of a conductive membrane and the rest of the capsule can be constructed of a biocompatible material. The capsule can include (within the capsule) a blocking electrode contact, a return electrode contact, and a powering/communication component. The blocking electrode contact can be configured to deliver a direct current (DC) through a portion of the conductive membrane. The DC can be configured to block conduction in the neural tissue to provide OD-ENB, either cathodic or anodic. The return electrode contact can be configured to receive a return current from the neural tissue through another portion of the conductive membrane. The powering/communication component can be configured to communicate with the power source to receive a power signal.

In another aspect, the present disclosure can include a method for electrically anesthetizing a peripheral nerve with OD-ENB for chronic pain management. The method can include wirelessly powering a capsule within a patient's body with a power signal from an external power source (which can power a plurality of capsules, in some embodiments). At least a portion of the capsule can be constructed of a conductive membrane, while the rest of the capsule can be constructed of a biocompatible material. The capsule can include a blocking electrode contact configured to deliver a DC through a portion of the conductive membrane, wherein the DC is configured to block conduction in the neural tissue to provide OD-ENB; a return electrode contact configured to receive a return current from the neural tissue through another portion of the conductive membrane; and a powering/communication component configured to communicate with the external power source to receive the power signal. The method can also include delivering the DC from the blocking electrode contact to the neural tissue for a time. The DC can be configured to cause the OD-ENB (either a cathodic block or an anodic block).

In still another aspect, the present disclosure can include a neuromodulation device that can be used to electrically anesthetize a peripheral nerve with on-demand electrical nerve block (OD-ENB) for chronic pain management. The neuromodulation device can include an implantable capsule, at least a portion of which can be constructed of a conductive membrane and the rest of the capsule can be constructed of a biocompatible material. The capsule can include within the capsule, a blocking electrode contact, a return electrode contact, and a powering/communication component. The blocking electrode contact can be configured to deliver a DC through a portion of the conductive membrane. The DC can be configured to block conduction in the neural tissue to provide OD-ENB (either a cathodic block or an anodic block). The return electrode contact can be configured to receive a return current from the neural tissue through another portion of the conductive membrane. The powering/communication component can be configured to communicate with one or more external components located external to the patient's body. One of the one or more external components can include an external power source that sends a power signal to the neuromodulation device that has no internal battery. The one or more external components can be used for powering/communication with a plurality of capsules.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
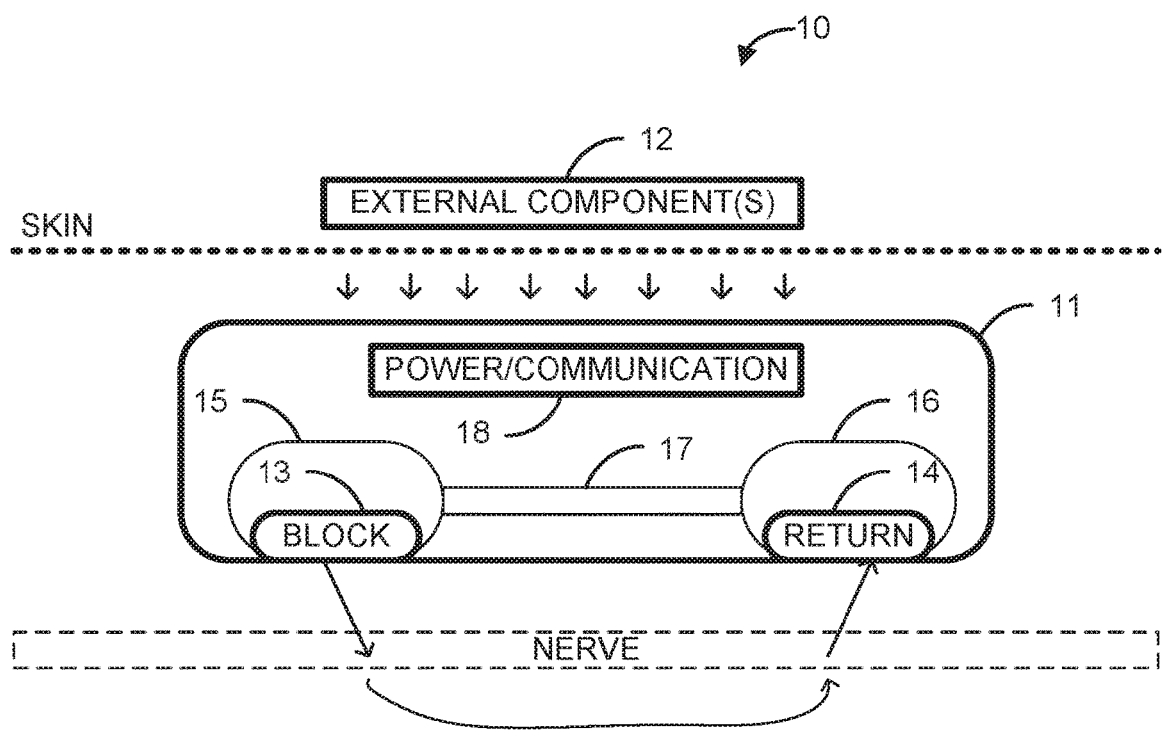
FIG. 1 is a schematic diagram showing an example of a system that can be used to electrically anesthetize a peripheral nerve with on-demand electrical nerve block (OD-ENB) for chronic pain management in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "on-demand electrical nerve block (OD-ENB)" is a means of electrically anesthetizing a peripheral nerve for the treatment of chronic pain and other disorders. OD-ENB can provide a patient the ability to suppress their pain symptoms (or symptoms of other disorders) immediately with no systemic side effects other than inactivation of the targeted nerve. The treatment is completely non-addicting and provides an alternative to pharmacological treatments. Additionally, dosing is not limited because there are no dose-related toxicity effects.

As used herein, the terms "electrical block", "electrical nerve block", "nerve conduction block", and "nerve block" (as well as variations thereof) can refer to the attenuation of conduction in one or more nerves within target neural tissue by a purposeful interference with nerve activation. The interference with nerve activation can be due to a change in the electric field caused by application of an electrical signal (to the neural tissue. Attenuating conduction can refer to extinguishing 100% (complete block) or less (partial block) (e.g., 90%, 80%, 70%, 60%, 50%, or the like) of the action potentials traveling through the target neural tissue. In some instances, the electrical block can be can be partial or complete and reversible. The electrical block can be a "hyperpolarization block" or a "depolarization block".

As used herein, the term "electrical signal" can refer to a time-varying voltage or current. As an example, the electrical signal can transmit a direct current (DC). For example, "DC block" can refer to the application of a DC pulse with an amplitude and polarity configured to cause a change in electric field (to depolarize or hyperpolarize) sufficient to alter conduction in the nerve.

As used herein, the term "direct correct (DC)" can refer to a type of electrical signal that includes a unidirectional flow of electric charge (e.g., varying in time, not amplitude). For example, the DC can have a plateau of a cathodic polarity or an anodic polarity. However, in some instances, at least a portion of the amplitude may vary—for example, the DC can further be represented as a waveform that includes a ramp from a zero position to the plateau and may also include a ramp down from the plateau position to the zero position. As another example, the waveform can include a subsequent plateau of the opposite polarity (in such cases, the waveform can be a biphasic waveform with the second phase configured to reduce charge either as a charge balanced waveform or a charge imbalanced waveform). The waveform can also include ramps from zero to the plateau and/or from the plateau to zero.

As used herein, a "waveform" can refer to a graphical representation of changes in current or voltage over time.

As used herein, the term "hyperpolarization block" or "anodic block" can refer to the cessation of nerve signaling in one or more nerves within target neural tissue caused by the accumulation of negative charges and/or loss of positive charges within a cell, lowering its membrane potential below its resting potential. For example, an influx of negative chloride ions or a loss of positive potassium ions can prevent the activation gates of voltage-gated sodium channels from opening, making action potentials more difficult to generate. An anodic (negatively charged) current can be used to cause a hyperpolarization block.

As used herein, the term "depolarization block" or "cathodic block" can refer to the cessation of nerve signaling in one or more nerves within target neural tissue caused by the accumulation of certain positively charged ions within a cell. For example, increased intracellular potassium ion levels can close inactivation gates in voltage-gated sodium channels within the cellular membrane, such that the movement of sodium into the cell is reduced and action potentials are inhibited. A cathodic (positively charged) current can be used to cause a depolarization block.

As used herein, the term "polarity" can refer to a direction of electron movement. For example, the polarity can be cathodic (positively charged) or anodic (negatively charged).

As used herein, the term "nerve" can refer to at least one or more fibers (e.g. axons) of nerve cells that employ electrical and chemical signals to transmit motor, sensory, and/or autonomic information from one body part to another. A nerve can refer to a component of the central nervous system and/or the peripheral nervous system. Additionally, one or more nerves can make up neural tissue.

As used herein, the terms "nerve activity" and "neural activity" can refer to signaling (conduction) and activation patterns to transmit neural signals carrying neural information.

As used herein, the term "conduction" can refer to movement of charged particles through space (e.g., a nerve fiber), forming an electrical current. Electrical block can be used to attenuate conduction through one or more nerves.

As used herein, the term "amplitude" can refer to a measurement of the dependent variable (e.g., current, voltage, etc.) above or below zero.

As used herein, the term "electrode contact" can refer to a material acting as a conductor through which electricity enters or leaves. At least a portion of the material can be a biocompatible material.

As used herein, the term "coil" can refer to an electric circuit element with one or more turns, usually roughly circular or cylindrical, of current-carrying wire designed to produce a magnetic field or provide electrical resistance or inductance.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

Chronic pain management is a complicated and highly patient specific area of medicine. Current pain management treatment modalities can include lifestyle changes, physical therapy, analgesics, opioids, anesthetic nerve block, radiofrequency ablation, and radical surgery. Current treatment modalities are ill suited to address the needs of patients in terms of at least adequate pain relief, quality of life, and convenience. Patients often feel as if their pain management is out of their control. There is a need for an effective pain treatment that allows patients to control their pain management, giving pain relief immediately when it is needed without having to visit a medical facility and without the use of addictive opioids.

The present disclosure describes devices, systems, and methods that provide on-demand electrical nerve block (OD-ENB), a self-administered patient specific treatment modality. OD-ENB is a treatment modality that gives immediate pain relief, so OD-ENB is well-suited for chronic pain management, but OD-ENB can also be used in the treatment of other disorders. OD-ENB is fast acting, reversible, non-addictive, localizable, titratable, non-addictive treatment modality that gas no side effects. Most notably, OD-ENB is minimally invasive, including an external device that includes a power source and an implantable capsule that receives power from the power source (e.g., through an inductive coupling that allows for communication and power transfer) and includes an electrode configuration to deliver a direct current to achieve the nerve block. The electrode configuration includes a blocking electrode contact configured to deliver the DC to block conduction in the neural tissue and a return electrode contact configured to receive a return current. The implantable capsule does not include an internal battery, allowing the size of the capsule to be reduced. It should be noted that external component can be used for powering/communication with a plurality of capsules (e.g., to provide a complete block to one or more nerves).

III. Systems

An aspect of the present disclosure can include a system 10 (FIG. 1) that can provide on-demand electrical nerve block (OD-ENB), which can be used for chronic pain management (and the treatment of other disorders). OD-ENB is a means of electrically anesthetizing a portion of neural tissue (that includes a peripheral nerve of interest), which can be used to treat a wide range of patients (spanning from younger individuals who are trying to maintain an active lifestyle to elderly individuals with potentially complicated medication needs). Due to the complicated nature of pain, it is difficult to find a solution that fits all patients, but OD-ENB is well suited to address the need for adequate pain relief of this wide spectrum of patients because OD-ENB can be customized in terms of dosage and/or location, providing adequate pain relief, quality of life, and convenience. Accordingly, OD-ENB gives patients the feeling that their pain management is controllable, since OD-ENB provides the patient the ability to immediately suppress pain symptoms. Further, because OD-ENB is based on the fundamental principle of electrical nerve block, there are no systemic side-effects other than the inactivation of the targeted nerve. The treatment is completely non-addicting and thus provides an excellent alternative to pharmacological treatments. In addition, dosing with the ON-ENB system is not limited because there are no dose-related toxicity effects. The OD-ENB can be provided using a DC waveform without production of irreversible Faradaic reaction products at the neural tissue via manipulation of the DC waveform and/or the electrode material.

The system 10 includes a neuromodulation device (referred to as an implantable capsule 11) and one or more external device(s) 12. The capsule 11 can be implanted at a distance under the patient's skin in proximity to a nerve of interest (e.g., including sensory nerves, like C fibers or other fibers associated with pain) to provide localized nerve block. In some instances, the capsule 11 can be injected into the patient's body next to the nerve of interest. The pain can be associated with any type of pain in the patient's body. Non-limiting examples can be pain associated with knee osteoarthritis (KOA), shoulder pain, pain associated with hernia repair, pelvic pain, and the like. The nerve of interest (or target nerve) related to these non-limiting examples can include the genicular nerve, the axillary nerve, the suprascapular nerve, the ilioinguinal nerve, the iliohypogastric nerve, the pudendal nerve, or the like.

The capsule 11 can be of a small size so that it can be implanted without substantially disrupting the patient's comfort. Additionally, at least a portion of the external shell of the capsule 11 can be made of one or more substantially biocompatible materials (e.g., at least a portion of the external shell can be made of a conducting portion, such as a biocompatible composite membrane). For example, the capsule 11 can be miniature. In some instances, the size of the capsule 11 can be small because the capsule 11 does not include an internal battery. In these instances, the capsule 11 can be externally powered under control of the patient by a power source, which can be one of the one or more external device(s) 12. In some instances, the one or more external components can be used for powering/communication with a plurality of capsules.

At least a portion of the capsule 11 can be configured to deliver a direct current (DC) to the target nerve to deliver a DC block (e.g., through a blocking electrode contact 13). For block, the DC can have an amplitude that is at least a block threshold. The block threshold for different types of nerves of different sizes may be different. The DC used for block can be cathodic (positively charged) with a cathodic amplitude of at least the cathodic block threshold or anodic (negatively charged) with an anodic amplitude of at least the anodic block threshold. The DC block can be provided as hyperpolarization block or depolarization block. Hyperpolarization block is caused by the accumulation of negative charges and/or loss of positive charges within a cell, lowering its membrane potential below its resting potential, caused by an anodic current. Depolarizing block is caused by the accumulation of certain positively charged ions within a cell, caused by a cathodic current. The DC used for block can be administered for a time. As a non-limiting example, the time can be more than 2 minutes. As another non-limiting example, the time can be more than 5 minutes. As yet another non-limiting example, the time can be more than 10 minutes.

The DC can be generated as a DC waveform with a shape that facilitates the DC block. In some instances, the generated DC waveform can have an anodic polarity or a cathodic polarity, and an amplitude sufficient to cause the DC block. As an example, the DC block can be delivered by a monophasic waveform or a biphasic waveform. As a further example, the waveform can have a ramp to the cathodic or anodic block threshold. In some instances, the properties of the DC waveform can be manipulated so that block can occur uninterrupted during the equal and opposite recharge phase.

The capsule 11 can include a blocking electrode 15 and a blocking electrode contact 13, a return electrode 16 and a return electrode contact 14, and a powering/communications component 18. In some instances, the blocking electrode 15 and the return electrode 16 can be sub-capsules within the larger capsule 11 that at least partially enclose the blocking electrode contact 13 and the return electrode contact 14. The sub-capsules include materials necessary for the electrode (e.g., saline, an ionically conductive medium, a high charge capacity material, a high capacitance slurry material, etc.). It should be noted that in some embodiments, the materials necessary for the blocking electrode 15 may be different from those required by the return electrode 16. For example, at least the blocking electrode 15 can be designed as described in at least one of U.S. Pat. No. 9,008,800, WO 2019/133783, WO 2019/133784, U.S. Pat. No. 9,387,322, or U.S. Pat. No. 10,195,434, which are incorporated herein by reference. In any of these examples, the electrode can convert the DC waveform into an ionic signal, which can be delivered to the target nerve by the blocking electrode contact 13. The blocking electrode contact 13 and the return electrode contact 14 can be located in any position in the capsule 11. For example, the blocking electrode contact 13 and the return electrode contact 14 can be located on the same side (e.g., next to each other) or on different sides (e.g., opposite one another) of the capsule 11. The sub-capsules can be connected by a channel 17 with a valve for recharging. In some instances, the valve of the channel 17 can be a microfluidic valve that can be used to provide a path for recharge so that the recharge can occur at a higher amplitude, resulting in a shorter recharge duration.

At least a portion of the external shell of the capsule can be made of a conducting portion, such as a biocompatible composite membrane. In some instances, the conducting portion can separate material(s) of the electrode from the tissue, while providing ionic conduction through the membrane. The conducting portion can be from 20% to 100% of the external shell. In some instances, the conducting portion can be noncontiguous. The remaining portion of the external shell can be a non-conductive or minimally-conductive biocompatible material. Additionally, the blocking electrode contact 13 and the return electrode contact 14 can be configured to deliver the DC to the nerve and receive the return current from the nerve through at least respective portions of the conductive membrane.

The powering/communications component 18 can be configured to communicate with one or more external component(s) 12 located external to the patient's body. Although not shown herein, the one or more external components 12 can be used for powering/communication of a plurality of capsules.

Figure 2:
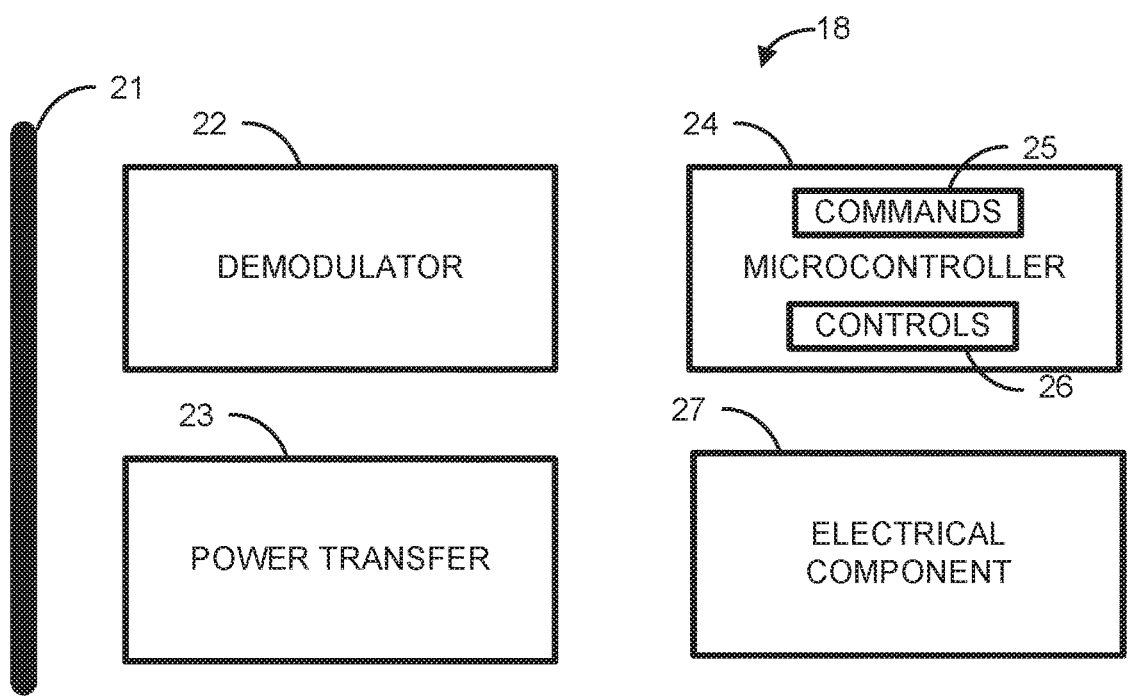
FIG. 2 shows an example of the power/communications component of FIG. 1.

As an example, both the powering/communications component 18 and the one or more external component(s) can each have an inductive coil for communication and/or power transfer of an inductive power signal. At least one of the one or more external component(s) 12 can include an external power source that sends a power signal to the powering/communications component 18. The powering/communications component 18 is shown in greater detail in FIG. 2, in which the powering/communications component 18 includes a communications component 21, a demodulator 22, a power transfer component 23, a microcontroller 24 with commands 25 and controls 26, as well as an electrical component 27.

The communications component 21 can be configured to communicate with the one or more external device(s) 12 outside of the patient's body. In some instances, the communications component 21 can be an inductive coil that is configured to communicate with an inductive coil located outside the patient's body. The communications component 21 can receive commands, like DC block set point commands and wireless power (or energy). The DC set point commands can go through the demodulator 22 to the microcontroller 24, which interprets the DC set point commands and sets commands 25 and controls 26 accordingly. The wireless power can be received by the power transfer component 23, which has a power transfer rectifier, shunt rectifier, and other components, and sent to the electrical component 27. Based on the wireless power, as well as the set point commands 25 and controls 26, the electrical component can configure the DC and deliver the DC to the blocking electrode 15 and/or the blocking electrode contact 13 for delivery to the neural tissue. Accordingly, the electrical component 27 can be coupled to the communications component 21 and the blocking electrode 15 and/or blocking electrode contact 13. In some instances, the electrical component can also be coupled to the return electrode 16 and/or the return electrode contact 14. The electrical component 27 can include a current-to-voltage charge pump-converter that can multiply the received voltage to provide enough compliance voltage for constant DC nerve block current. A switch network can be used to change DC block polarity if necessary and to periodically shunt power from the communication link (e.g., inductive link) with the communications component 21 to an actuator associated with the valve of the channel 17 for repolarization.

IV. Methods

Figure 3:
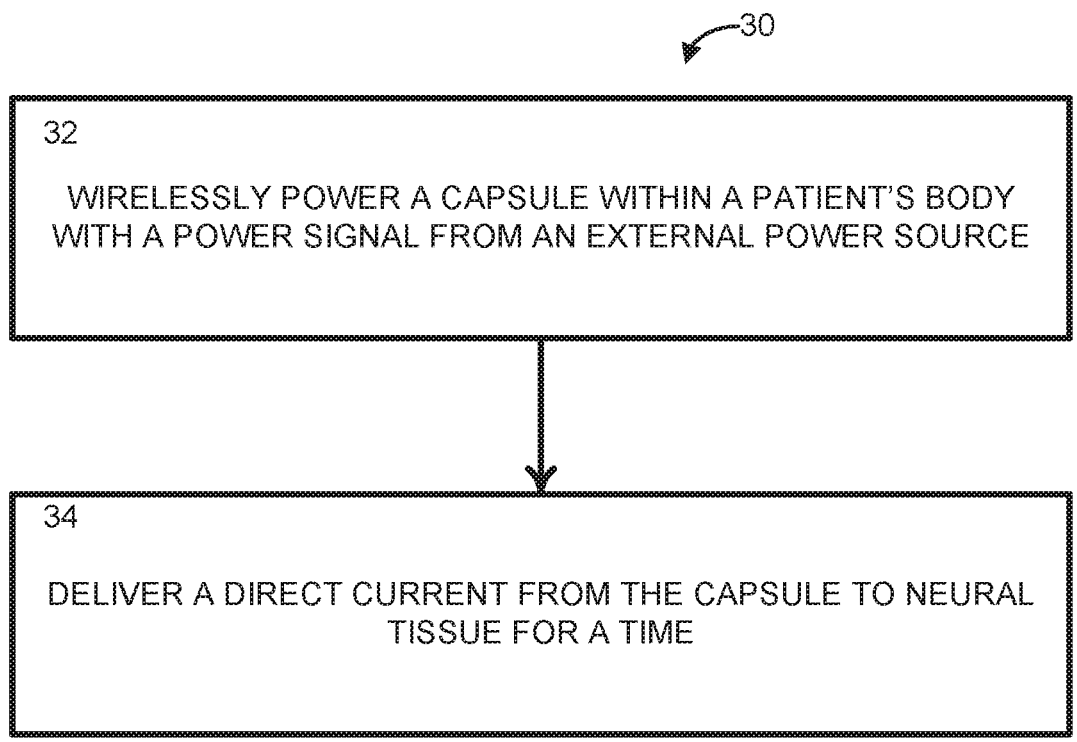
FIG. 3 is a process flow diagram illustrating a method for electrically anesthetizing a peripheral nerve with OD-ENB for chronic pain management in accordance with another aspect of the present disclosure.

Another aspect of the present disclosure can include a method 30 for electrically anesthetizing a peripheral nerve with on-demand electrical nerve block (OD-ENB) for chronic pain management (and/or the treatment of other disorders), as shown in FIG. 3. The method 30 can be executed using the system 10 shown in FIG. 1. The implantable capsule 11 delivers the OD-ENB to the patient using the blocking electrode 15 and blocking electrode contact 13 configured to deliver a direct current (DC) to a neural tissue (e.g., including one or more C fibers associated with pain) to block conduction, the return electrode 16 and return electrode contact 14 configured to receive the return DC from the nerve, and powering/communications component 18 configured to communicate with at least one external device 12 to at least receive a power signal. The implantable capsule 11 does not include a battery, causing the implantable capsule 11 to be of a smaller size. Additionally, at least the blocking electrode contact 13, as well as the blocking electrode 15 in some instances, are designed to avoid Faradaic reactions, like hydrogen evolution, oxygen evolution, chlorine evolution, or the like, when delivering the DC to the neural tissue. For example, the blocking electrode 15 can utilize a saline interface. As another example, the blocking electrode 15 can utilize high capacitance electrode materials. Specific examples of electrodes that can be used as the blocking electrode 15 include a separated interface nerve electrode (SINE), a carbon coated platinum electrode, a woven cloth carbon electrode, a carbon slurry electrode, or the like.

For purposes of simplicity, the method 30 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 30, nor is the method 30 necessarily limited to the illustrated aspects.

At Step 32, the capsule (e.g., implantable capsule 11, at least a portion of the capsule constructed of a conductive membrane and the rest of the capsule comprises a biocompatible material) can be wirelessly powered within the patient's body from an external power source (e.g., within external component(s) 12). The powering/communications component 18 can be configured to communicate with the external power source to receive the power signal. Note that the external component can be used for powering/communication with a plurality of capsules. The powering/communications component 18 can also be configured to receive and/or transmit information to the external component(s) 12 (as shown and described with respect to FIG. 2). In some instances, the implantable capsule 11 can be injected into the patient's body in proximity to a target nerve (which can be chosen based on the condition causing pain).

At Step 34, the DC (either cathodic or anodic) can be delivered from the capsule (e.g., implantable capsule 11) to neural tissue for a time. The DC can provide the OD-ENB for at least the time. In some instances, the OD-ENB can last for a time period after the OD-ENB is turned off. In other instances, the OD-ENB can be reversed quickly. The blocking electrode contact 13 can be configured to deliver the DC (configured to block conduction in the neural tissue to provide the OD-ENB) through a portion of the conductive membrane. In some instances, the blocking electrode 15 can convert the DC to an ionic current delivered by the blocking electrode contact 13. The return electrode contact 14 can be configured to receive a return current from the neural tissue through another portion of the conductive membrane after the DC is applied.

From the above description, those skilled in the art will perceive improvements, changes and modifications. Such improvements, changes and modifications are within the skill of one in the art and are intended to be covered by the appended claims.

The following is claimed:

1. A neuromodulation device comprising:
an implantable capsule having an external shell, wherein the external shell comprises a portion comprising a biocompatible material and another portion comprising a conductive membrane, wherein the capsule comprises:
  a blocking electrode contact configured to deliver a direct current (DC) through a portion of the conductive membrane, wherein the DC is configured to block conduction in the neural tissue to provide on demand electrical nerve block (OD-ENB), wherein the OD-ENB provides a cathodic block or an anodic block;
  a return electrode contact configured to receive a return current from the neural tissue through another, non-contiguous portion of the conductive membrane; and
  a powering/communication component configured to communicate with one or more external components located external to the patient's body, wherein one of the one or more external components comprises an external power source that sends a power signal to the neuromodulation device that has no internal battery.

2. The neuromodulation device of claim 1, wherein the blocking electrode contact and the return electrode contact are each at least partially enclosed in sub-capsules within the capsule that are connected by a channel for recharging.

3. The neuromodulation device of claim 2, wherein at least the blocking electrode contact comprises a high charge capacity material, a high capacitance slurry, or an ionically conductive medium within the associated sub-capsule.

4. The neuromodulation device of claim 3, wherein the OD-ENB is provided without production of irreversible Faradaic reaction products at the neural tissue.

5. The neuromodulation device of claim 1, wherein the powering/communication component comprises an inductive coil and the external power source comprises another inductive coil, wherein the power signal is an inductive power signal.

6. The neuromodulation device of claim 5, wherein the capsule further comprises an electrical component coupled to the inductive coil, the blocking electrode contact, and the return electrode contact.

7. The neuromodulation device of claim 6, wherein the electrical component configures the DC and delivers the DC to the blocking electrode contact.

8. The neuromodulation device of claim 1, wherein the DC is delivered to the neural tissue as an ionic current, wherein a blocking electrode converts the DC to the ionic current delivered by the blocking electrode contact.

9. The neuromodulation device of claim 1, wherein the blocking electrode contact and the return electrode contact are located on a same side of the capsule or opposite sides of the capsule.

10. A system comprising:
an external power source; and
an implantable capsule having an external shell, wherein the external shell comprises a portion comprising a biocompatible material and another portion comprising a conductive membrane, wherein the capsule comprises:
  a blocking electrode contact configured to deliver a direct current (DC) through a portion of the conductive membrane, wherein the DC is configured to block conduction in the neural tissue to provide on demand electrical nerve block (OD-ENB), wherein the ON-ENB is cathodic or anodic;
  a return electrode contact configured to receive a return current from the neural tissue through another, non-contiguous portion of the conductive membrane; and
  a powering/communication component configured to communicate with the power source to receive a power signal.

11. The system of claim 10, wherein the power source is external to the patient's body and the capsule comprises no internal power source.

12. The system of claim 11, wherein the wireless charging component comprises an inductive coil and the power source external to the patient's body comprises another inductive coil, wherein the power signal is an inductive power signal.

13. The system of claim 12, wherein the capsule further comprises an electrical component coupled to the inductive coil, the blocking electrode contact, and the return electrode contact.

14. The system of claim 13, wherein the electrical component configures the DC and delivers the DC to the blocking electrode contact.

15. The system of claim 11, wherein the blocking electrode contact and the return electrode contact are each at least partially enclosed in sub-capsules within the capsule that are connected by a channel for recharging.

16. The system of claim 15, wherein at least a blocking electrode and/or the blocking electrode contact comprises a high charge capacity material, a high capacitance slurry, or an ionically conductive medium within the associated sub-capsule.

* * * * *